(12) United States Patent
Turkson

(10) Patent No.: US 8,685,941 B2
(45) Date of Patent: Apr. 1, 2014

(54) DRUG COMPOSITION CYTOTOXIC FOR PANCREATIC CANCER CELLS

(75) Inventor: James Turkson, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 116 days.

(21) Appl. No.: 13/131,840

(22) PCT Filed: Nov. 30, 2009

(86) PCT No.: PCT/US2009/066079
§ 371 (c)(1),
(2), (4) Date: Jun. 27, 2011

(87) PCT Pub. No.: WO2010/065444
PCT Pub. Date: Jun. 10, 2010

(65) Prior Publication Data
US 2011/0263525 A1  Oct. 27, 2011

Related U.S. Application Data

(60) Provisional application No. 61/118,792, filed on Dec. 1, 2008, provisional application No. 61/249,307, filed on Oct. 7, 2009.

(51) Int. Cl.
*A61K 31/70* (2006.01)
(52) U.S. Cl.
USPC .......................................................... 514/49
(58) Field of Classification Search
None
See application file for complete search history.

(56) References Cited

U.S. PATENT DOCUMENTS

| 5,770,599 | A * | 6/1998 | Gibson ....................... 514/228.2 |
| 6,596,746 | B1 * | 7/2003 | Das et al. ....................... 514/370 |
| 2006/0293264 | A1 | 12/2006 | Grandis et al. ............... 536/24.5 |
| 2007/0010428 | A1 | 1/2007 | McMurray ....................... 514/2 |
| 2007/0286864 | A1 | 12/2007 | Buck .......................... 424/130.1 |

FOREIGN PATENT DOCUMENTS

| WO | WO 2008/077062 | 6/2008 |
| WO | WO 2009/036101 | 3/2009 |
| WO | WO 2010/065444 | 6/2010 |

OTHER PUBLICATIONS (R) M. J. O'Neil et al. (eds.), "The Merck Index, 14th Edition," Merck & Co., Whitehouse Station, NJ, 2006, only pp. 478 & 754 supplied (see "dasatinib," No. 2829 and "ZD1839," No. 4379, respectively).*

(S) SigmaAldrich.com/catalog; "Tyrphostin AG 490" and "S3I-201," data pages including chemical structures; Google internet searches on Oct. 29, 2013 with the search terms <AG 490> and <S3I-201>.*

Communication conveying extended European Search Report for EP Application No. 09830921.4-2123 issued May 3, 2012, which claims priority to PCT/US2009/066079 filed on Nov. 30, 2009 (Applicants—University of Central Florida Research Foundation // Inventor—James Turkson) (14 pages); Mar. 5, 2012.

International Preliminary Report on Patentability issued on Jun. 7, 2011 for PCT Application No. PCT/US2009/066079 filed on Nov. 30, 2009 (Applicants—University of Central Florida Research Foundation // Inventor—James Turkson) (5 pages) Mar. 24, 2010.

Written Opinion issued on Mar. 24, 2010 for PCT Application No. PCT/US2009/066079 filed on Nov. 30, 2009 (Applicants—University of Central Florida Research Foundation // Inventor—James Turkson) (4 pages) Mar. 24, 2010.

International Search Report issued on Jun. 10, 2010 for PCT Application No. PCT/US2009/066079 filed on Nov. 30, 2009 (Applicants—University of Central Florida Research Foundation // Inventor—James Turkson) (2 pages) Mar. 24, 2010.

Huang C, et al. (2006) Inhibition of STAT3 activity with AG490 decreases the invasion of human pancreatic cancer cells in vitro. Cancer Sci. 97(12): 1417-1423.

Jaganathan S, et al. (2009) Physical and functional association of EGFR, Src and Stat3 promotes aberrant Stat3 activity and supports growth, survival, migration and invasion of pancreatic cancer cells. Proc Am Assoc Cancer Res. 50: 423.

Jaganathan S, et al. (2010) Enhanced sensitivity of pancreatic cancer cells to concurrent inhibition of aberrant signal transducer and activator of transcription 3 and epidermal growth factor receptor or Src. J Pharmacol Exp Ther. 333(2): 373-381.

Kim H, et al. (2006) Inhibition of Stat3 overcomes gefitinib resistance cause by T790M mutation of EGFR tyrosine kinase. 4(12): 55. Nov. 7-10, 2006. Poster 174. 18th Symposium on Molecular Targets and Cancer Therapeutics.

Moore MJ, et al. (2007) Erlotinib plus gemcitabine compared with gemcitabine alone in patients with advanced pancreatic cancer: a phase III trial of the National Cancer Institute of Canada Clinical Trials Group. J Clin Oncol. 25(15): 1960-1966.

Siddiquee K, et al. (2007) Selective chemical probe inhibitor of Stat3, identified through structure-based virtual screening, induces antitumor activity. Proc Natl Acad Sci USA. 104(18): 7391-7396.

Siddiquee K, et al. (2008) STAT3 as a target for inducing apoptosis in solid and hematological tumors. Cell Res. 18(2): 254-267.

Bild Ah, et al. (2002) Cytoplasmic transport of Stat3 by receptor-mediated endocytosis. Embo J. 21: 3255-3263.

(Continued)

*Primary Examiner* — Lawrence E Crane
(74) *Attorney, Agent, or Firm* — Ballard Spahr LLP

(57) ABSTRACT

Disclosed herein are compositions comprising a drug combination that comprises ZD and S3I-201, Das and S3I-201, ZD and AG490, or Das and AG490. The disclosed drug combinations target two or more functional elements such as EGFR or Src and Stat3 or Jaks in pancreatic cancer cells. Also disclosed herein are methods of using the disclosed compositions to cytotoxically affect pancreatic cancer cells and methods of making the disclosed compositions.

10 Claims, 6 Drawing Sheets

(56) References Cited

OTHER PUBLICATIONS

Biscardi J, et al. (1999) c-Src-mediated phosphorylation of the epidermal growth factor receptor on Tyr845 and Tyr1101 is associated with modulation of receptor function. J Biol Chem. 274: 8335-8343.
Brabek J, et al. (2004) CAS promotes invasiveness of Src transformed cells. Oncogene. 23: 7406-7415.
Burris HR and Rocha-Lima C. (2008) New therapeutic directions for advanced pancreatic cancer: targeting the epidermal growth factor and vascular endothelial growth factor pathways. Oncologist. 13: 289-298.
Cao X, et al. (1996) Activation and association of Stat3 with Src in v-Src-transformed cell lines. MolCell Biol. 16: 1595-1603.
Coffer PJ, and Kruijer W. (1995) EGF receptor deletions define a region specifically mediating STAT transcription factor activation. Biochem Biophys Res Commun. 210: 74-81.
Darnell JE, Jr. (1997) STATs and gene regulation. Science. 277: 1630-1635.
Darnell JE. (2005) Validationg Stat3 in cancer therapy. Nat Med. 11: 595-596.
DeArmond D, et al. (2003) Autocrine-mediated ErbB-2 kinase activation of STAT3 is required for growth factor independence of pancreatic cancer cell lines. Oncogene. 22: 7781-7795.
Dong M, et al. (1998) Epidermal growth factor and its receptor as prognostic indicators in Chinese patients with pancreatic cancer. Anticancer Res. 18(6B): 4613-4619.
Downward J, et al. (1984) Autophosphorylation sites on the epidermal growth factor receptor. Nature. 311: 483-485.
Dugan MC, et al. (1997) HER-2/neu expression in pancreatic adenocarcinoma: relation to tumor differentiation and survival. Pancreas. 14: 229-236.
Garcia R, et al. (2001) Constitutive activation of Stat3 by the Src and JAK tyrosine kinases participates in growth regulation of humna breast carcinoma cells. Oncogene. 20: 2499-2513.
Gouillex F, et al. (1995) Prolactin and interleukin-2 receptors in T lymphocytes signal through MGF-STAT5-like transcription factor. Endocrinology. 136: 5700-5708.
Grandis JR, et al. (2000) Epidermal growth factor receptor-mediated stat3 signaling blocks apoptosis in head and neck cancer. Laryngoscope. 110: 868-874.
Huang M, et al. (2002) Inhibition of Bcr-Abl kinase activity by PD180970 blocks constitutive activation of Stat5 and growth of CL cells. Oncogene. 21: 8804-8816.
Irby RN, et al. (1999) Activating SRC mutation in a subset of advanced human colon cancers. Nat Genet. 21: 187-190.
Ishizawar R and Parsons SJ. (2004) c-Src and cooperating partners in human cancer. Cancer Cell. 6: 209-214.
Jimeno A, et al. (2008) Coordinated epidermal growth factor receptor pathway gene overexpression predicts epidermal growth factor receptor pathway gene overexpression predicts epidermal growth factor receptor inhibitor sensitivity in pancreatic cancer. Cancer Res. 68: 2841-2849.
Johnson FM, et al. (2007) Abrogation of signal transducer and activator of transcription 3 reactivation after Src kinase inhibition results in synergistic antitumor effects. Clin Cancer Res. 13: 4233-4244.
Korc M, et al. (1986) Enhanced expression of epidermal growth factor receptor correlates with alternations of chromosome 7 in human pancreatic cancer. Proc Natl Acad Sci USA. 83: 5141-5144.
Kotha A, et al. (2006) Resveratrol inhibits Src and Stat3 signaling and induces apoptosis of malignant cells containing activated Stat3 protein. Mol Cancer Ther. 5: 621-629.
Krueger JG, et al. (1980) Differences in intracellular location of pp60src in rat and chicken cells transformed by Rous sarcoma virus. Proc Natl Acad Sci USA. 77: 4142-4146.
Lo HW, et al. (2005) Nuclear interaction of EGFR and STAT3 in the activation of the iNOS/NO pathway. Cancer Cell. 7: 575-589.
Lutz MP, et al. (1998) Overexpression and Activation of the Tyrosine Kinase Src in Human Pancreatic Carcinoma. Biochem Biophys Res Commun. 243: 503-508.

Maa MC, et al. (1995) Potentiation of epidermal growth factor receptor-mediated oncogenesis by cSrc: implications for the etiology of multiple human cancers. Proc Natl Acad Sci USA. 92: 6981-6985.
Mahtouk K, et al. (2005) Expression of EGF-family receptors and amphiregulin in multiple myelome. Amphiregulin is a growth factor for myeloma cells. Oncogene. 24: 3512-3524.
Margolis B, et al. (1990) The tyrosine phosphorylated carboxy terminus of the EGF receptor is a binding site for GAP and PLC-gamma. EMBO J. 9: 4375-4380.
Nam S, et al. (2005a) Indirubin derivatives inhibit Stat3 signaling and induce apoptosis in human cancer cells. Proc Natl Acad Sci USA. 102: 5998-6003.
Nam S, et al. (2005b) Action of the Src family kinase inhibitor, dasatinib (BMS-354825), on human prostate cancer cells. Cancer Res. 65: 9185-9189.
Ouyang H, et al. (2000) Immortal human pancreatic duct epithelial cell lines with near normal genotype and phenotype. Am J Pathol. 157: 1623-1631.
Parsons JT, et al. (1997) Src family protein tyrosine kinases: cooperating with growth factor and adhesion signaling pathways. Curr Opin Cell Biol. 9: 187-192.
Parsons JT. (2003) Focal adhesion kinase: the first ten years. J Cell Sci. 116: 1409-1416.
Philip PA. (2008) Targeted therapies for pancreatic cancer. Gastrointest Cancer Res. 2(Suppl2): S19-S19.
Ren Z and Shaefer TS. (2002) ErbB-2 activates Stat3 alpha in a Src- and JAK2-dependent manner. J Biol Chem. 8: 38486-38493.
Saif MW. (2008) Erlotinib: the first biologic in the management of pancreatic cancer. Expert Opin Pharmacother. 9: 1595-1607.
Salomon DS, et al. (1995) Epidermal growth factor-related peptides and their receptors in human malignancies. Crit Rev Oncol Hematol. 19: 183-232.
Sartor CI, et al. (1997) Role of epidermal growth factor receptor and STAT-3 activation in autonomous proliferation of SUM-102PT human breast cancer cells. Cancer Res. 57: 978-987.
Schlessinger J. (2000) Cell signaling by receptor tyrosine kinases. Cell. 103: 211-225.
Scholz ASH, et al. (2003) Activated signal transducer and activator of transcription 3 (STAT3) supports the malignant phenotype of human pancreatic cancer. Gastroenterology. 125: 891-905.
Seidel HM, et al. (1995) Spacing of palindromic half sites as a determinant of selective STAT (signal transducers and activators of transcription) DNA binding and transcriptional activity. Proc Natl Acad Sci USA. 92: 3041-3045.
Senderowicz AM, et al. (2007) Erlotinib/gemcitabine for first-line treatment of locally advanced or metastatic adenocarcinoma of the pancreas. Oncology (Williston Park). 21: 1696-706; discussion 1706-9, 1712, 1715.
Shao H, et al. (2003) Identification and characterization of signal transducer and activator of transcription 3 recruitment sites within the epidermal growth factor receptor. Cancer Res. 63: 3923-3930.
Shin NY, et al. (2004) Subsets of the major tyrosine phosphorylation sites in Crk-associated substrate (CAS) are sufficient to promote cell migration. J Biol Chem. 279: 38331-38337.
Shor AC, et al. (2007) Dasatinib inhibits migration and invasion in diverse human sarcoma cell lines and induces apoptosis in bone sarcoma cells dependent on SRC kinase for survival. Cancer Res. 67: 2800-2808.
Siddiquee K, et al. (2007b) An oxazole-based small-molecule Stat3 inhibitor modulates Stat3 stability and processing and induces antitumor cell effects. ACS Chem Biol. 2: 787-798.
Song JI and Grandis JR. (2000) STAT signaling in head and neck cancer. Oncogene. 19: 2489-2495.
Song L, et al. (2003) Activation of Stat3 by receptor tyrosine kinases and cytokines regulates survival in human non-small cell carcinoma cells. Oncogene. 22: 4150-4165.
Song L, et al. (2006) Dasatinib (BMS-354825) selectively induces apoptosis in lung cancer cells dependent on epidermal growth factor receptor signaling for survival. Cancer Res. 66: 5542-5548.
Summy JM., et al. (2003) Src family kinases in tumor progression and metastasis. Cancer Metastasis Rev. 22: 337-358.

(56) References Cited

OTHER PUBLICATIONS

Thelemann A, et al. (2005) Phosphotyrosine signaling networks in epidermal growth factor receptor overexpressing squamous carcinoma cells. Mol Cell Proteomics. 4: 356-376.

Tice JG, et al. (1999) Mechanism of biological synergy between cellular Src and epidermal growth factor receptor. Proc Natl Acad Sci USA. 96: 1415-1420.

Toyonaga T, et al. (2003) Blockade of constitutively activated Janus kinase/signal transducer and activator of transcription-3 pathway inhibits growth of human pancreatic cancer. Cancer Lett. 201: 107-116.

Trevino JG, et al. (2006) Src activation of Stat3 is an independent requirement from NF-kappaB activation for constitutive IL-8 expression in human pancreatic adeno carcinoma cells. Angiogenesis. 9: 101-110.

Trevion JG, et al. (2006) Inhibition of SRC expression and activity inhibits tumor progression and metastasis of human pancreatic adenocarcinoma cells in an orthotopic nude mouse model. Am J Pathol. 168: 962-972.

Turkson J, et al (2005) A novel platinum compound inhibits constitutive Stat3 signaling and induces cell cycle arrest and apoptosis of malignant cells. J Biol Chem. 280: 32979-32988.

Turkson J, et al. (1998) Stat3 activation by Src induces specific gene regulation and is required for cell transformation. Mol Cell Biol. 18: 2545-2552.

Turkson J, et al. (1999) Requirement for Ras/Rac 1-mediated p38 and c-Jun N-terminal kinase signaling in Stat3 transcriptional activity induced by the Src oncoprotein. Mol Cell Biol. 19: 7519-7528.

Turkson J, et al. (2001) Phosphotyrosyl peptides block Stat3-mediated DNA binding activity, gene regulation, and cell transformation. J Biol Chem. 276: 45443-45455.

Turkson J, et al. (2004a) Novel peptidomimetic inhibitors of signal transducer and activator of transcription 3 dimerization and biological activity. Mol Cancer Ther. 3: 261-269.

Turkson J, et al. (2004b) Inhibition of constitutive signal transducer and activator of transcription 3 activation by novel platinum complexes with potent antitumor activity. Mol Cancer Ther. 3: 1533-1542.

Turkson J. (2004) Stat proteins as novel targets for cancer drug discovery. Expert Opin Ther Targets. 8: 409-422.

Tzeng CW, et al. (2007) EGFR genomic gain and aberrant pathway signaling in pancreatic cancer patients. J Surg Res. 143: 20-26.

Ueda S, et al. (2004) The correlation between cytoplasmic overexpression of epidermal growth factor receptor and tumor aggressiveness: poor prognosis in patients with pancreatic ductal adenocarcinoma. Pancreas. 29: el-8.

Uegaki K, et al. (1997) Clinicopathological significance of epidermal growth factor and its receptor in human pancreatic cancer. Anticancer Res. 17(5B): 3841-3847.

Wagner BJ, et al. (1990) The SIF binding element confers sis/PDGF inducibility onto the c-fos promoter. EMBO J. 9: 4477-4484.

Wakeling AE, et al. (2002) ZD1839 (Iressa): an orally active inhibitor of epidermal growth factor signaling with potential for cancer therapy. Cancer Res. 62: 5749-5754.

Wu W, et al. (2002) Src-dependent phosphorylation of the epidermal growth factor receptor on tyrosine 845 is required for zinc-induced Ras activation. J Biol Chem. 277: 24252-24257.

Xie TX, et al. (2004) Stat3 activation regulates the expression of matrix metalloproteinase-2 and tumor invasion and metastasis. Oncogene. 23: 3550-3560.

Yang S, et al. (2008) Ligand-independent phosphorylation of Y869 (Y845) links mutant EGFR signaling to stat-mediated gene expression. Exp Cell Res. 314: 413-419.

Yokoi K, et al. (2005) Simultaneous inhibition of EGFR, VEGFR, and platelet-derived growth factor receptor signaling combined with gemcitabine produces therapy of human pancreatic carcinoma and prolongs survival in an orthotopic nude mouse model. Cancer Res. 65: 10371-10380.

Yu H, et al. (2004) the STATs of cancer—new molecular targets come of age. Nat Rev Cancer. 4: 97-105.

Yue P, et al. (2009) Targeting STAT3 in cancer: how successful are we? Expert Opin Investig Drugs. 18: 45-56.

Zhang J, et al. (2007) SRC-family kinases are activated in non-small cell lung cancer and promote the survival of epidermal growth factor receptor-dependent cell lines. Am J Pathol. 170: 366-376.

Zhang Y, et al. (2000) Activation of Stat3 in v-Src-transformed fibroblasts requires cooperation of Jak1 kinase activity. J Biol Chem. 275: 24935-24944.

Zhao S., et al. (2008) Inhibition of STAT3 Tyr705 phosphorylation by Smad4 suppresses transforming growth factor beta-mediated invasion and metastasis in pancreatic cancer cells. Cancer Res. 68: 4221-4228.

Noting of loss of rights pursuant to Rule 112(1) EPC issued on Jan. 10, 2013 for European Patent Application No. 09830921.4-2123, which claims priority to PCT/US2009/066079 filed on Nov. 30, 2009 (Applicant—University of Central Florida Research Foundation // Inventor—James Turkson) (2 pages).

\* cited by examiner

DRUG COMPOSITION CYTOTOXIC FOR PANCREATIC CANCER CELLS

CROSS-REFERENCE TO RELATED APPLICATIONS

This application is a national phase application of International Application No. PCT/US2009/066079, which was filed on 30 Nov. 2009, which claims priority to U.S. provisional application Ser. No. 61/118,792, which was filed on 1 Dec. 2008, and to U.S. provisional application Ser. No. 61/249,307, which was filed on 7 Oct. 2009, each application of which is incorporated herein by reference in its entirety.

STATEMENT REGARDING FEDERALLY SPONSORED RESEARCH OR DEVELOPMENT

The invention was made with government support under ROI CA106439 awarded by the National Institutes of Health. The government has certain rights in the invention.

FIELD OF THE INVENTION

The present invention relates to the field of drug development and, more particularly, to a drug composition cytotoxic for pancreatic cancer cells.

BACKGROUND OF THE INVENTION

Pancreatic cancer is a lethal disease with a poor prognosis and a mortality rate nearly the same as the rate of incidence. Moreover, the disease remains poorly understood. Multiple signal transduction proteins are activated during pancreatic ductal cell carcinogenesis, some may be secondary events, while many others might have critical roles and collectively contribute to the maintenance and the progression of the disease and its responsiveness to therapy. One of the major molecular abnormalities is the overexpression and/or activation of the EGFR protein, which has an incidence of 30-50% of pancreatic cancer cases (1). Evidence indicates that the hyperactive EGF/EGFR duo is important in the disease maintenance and progression (2). Similarly, the overexpression of the c-Src tyrosine kinase occurs in a large percentage of pancreatic adenocarcinoma and is observed to augment EGFR activities during tumorigenesis (3, 4). The over-activity of Src family kinases leads to deregulation of tumor cell growth and survival, disruption of cell-to-cell contacts, and the promotion of migration and invasiveness, and the induction of tumor angiogenesis (4, 5).

Another molecular abnormality is the aberrant activation of Stat3, a member of the Signal Transducer and Activator of Transcription (STAT) family of cytoplasmic transcription factors, which has also been detected in pancreatic tumors and tumor cell lines and been implicated in the disease (6-9). Stat3, as are the other STATs, requires extrinsic tyrosine phosphorylation to become activated and this is induced by growth factor receptors and cytoplasmic tyrosine kinases, such as Src and Janus kinase (Jaks) families (10). In contrast to normal STAT signaling that is transient in accordance with the requirements for normal biological processes, tumor cells harbor aberrant Stat3 activation. Studies show that aberrant Stat3 dysregulates cell growth and survival, promotes tumor angiogenesis, cell migration and invasion, and induces tumor immune tolerance (11-13).

De-regulated signal transduction provides the framework for functional cooperativity and signaling cross-talk that would not only support the malignant phenotype and the disease progression, but also influence the drug responsiveness. Within the context of the concurrent activation of EGFR, Src and Stat3 in pancreatic cancer, the potential for cooperation between EGFR and Src kinases to induce aberrant Stat3 activation and to cooperate in support of the cancer phenotype is a reasonable model to propose. Knowledge of this functional relationship and the collective roles of the proteins in supporting pancreatic cancer can facilitate the design of effective, multiple-targeted therapy for disease. We provide evidence that EGFR and Src promote constitutive Stat3 activation, with a compensatory Stat3 activation mechanism from Jaks, and together support the pancreatic cancer phenotype. Importantly, our study identifies that the concurrent inhibition of aberrant Stat3 and EGFR or Src is more effective in inducing antitumor cell response and pancreatic tumor regression in xenografts.

SUMMARY OF THE INVENTION

With the foregoing in mind, the present invention advantageously provides a cytotoxic composition containing a drug combination targeting two or more functional elements in pancreatic cancer cells, the functional elements comprising EGFR or Src and Stat3 or Jaks. A preferred embodiment of the cytotoxic composition is one wherein the drug combination contained therein is selected from ZD and S3I-201, Das and S31-201, ZD and AG490, Das and AG490, and combinations thereof. Furthermore, the preferred cytotoxic composition is that wherein the drug combination inhibits said functional elements at substantially the same time. The preferred composition of the present invention may also comprise a nucleoside analog inhibitory for DNA replication, for example, Gemcitabine.

The invention herein disclosed also includes a method of cytotoxically affecting (which could result in killing) pancreatic cancer cells, the method comprising contacting the cells with a drug combination which inhibits two or more cellular functional elements, the functional elements including EGFR or Src and Stat3 or Jaks. The method of the invention also includes an embodiment wherein the drug combination is selected from ZD and S31-201, Das and S31-201, ZD and AG490, Das and AG490, and combinations thereof. A preferred method of the invention also includes contacting the cells with a drug combination further comprising a nucleoside analog inhibitory for DNA replication, the nucleoside analog preferably being Gemcitabine.

The invention additionally includes a method of making a therapeutic medication cytotoxic for pancreatic cancer cells, the method comprising preparing a pharmaceutically acceptable composition containing a drug combination selected from ZD and S31-201, Das and S31-201, ZD and AG490, Das and AG490, and combinations thereof. The method of making the medication preferably also includes an embodiment wherein the drug combination further comprises a nucleoside analog inhibitory for DNA replication, for example, Gemcitabine.

BRIEF DESCRIPTION OF THE DRAWINGS

Some of the features, advantages, and benefits of the present invention having been stated, others will become apparent as the description proceeds when taken in conjunction with the accompanying drawings in which.

DETAILED DESCRIPTION OF PREFERRED EMBODIMENTS

Figure 1:
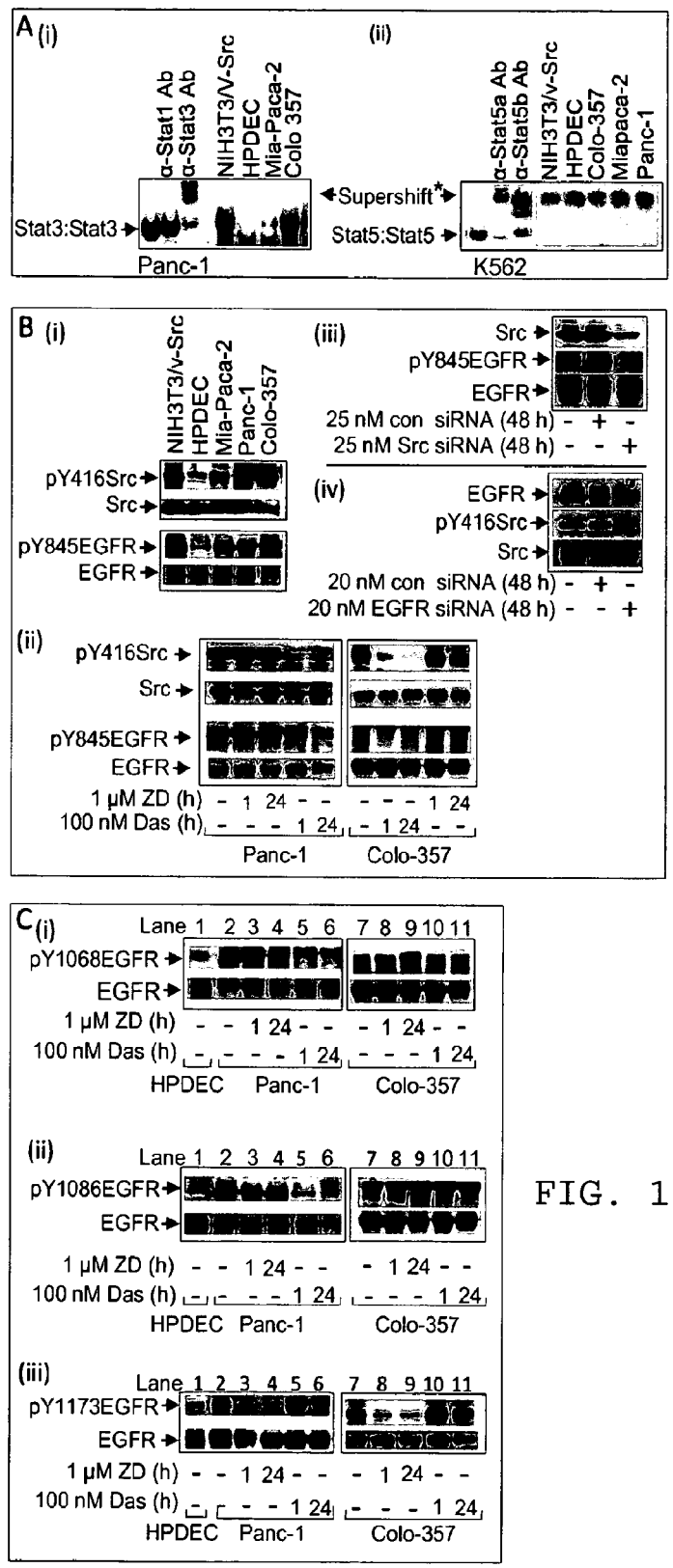
FIG. 1 shows EMSA and immunoblotting analyses of Stat3, Src and EGFR activities for effects of inhibitors. (A) EMSA analysis of STAT DNA-binding activity using (i) high-affinity sis-inducible element (hSIE) probe that binds Stat3 and Stat1 or (ii) mammary gland factor element (MGFe) probe that binds Stat1 or Stat5; and (B and C) Immunoblotting analysis of whole-cell lysates from cells (B) (i) untreated or (ii) treated with ZD 1839 (ZD), or Dasatinib (Das), or transfected with or without (iii) Src siRNA, (iv) EGFR siRNA, or scrambled siRNA control (con) and probing for pY416c-Src (pY416Src), Src, pY845EGFR, and EGFR; and (C) untreated or treated with ZD or Das and probing for (i) pY1068EGFR, (ii) pY1086EGFR and (iii) pY1173EGFR, and EGFR. Positions of STAT:DNA complexes in gel are shown; *Supershifts were performed with antibodies specifically recognizing either Stat1 (a-Stat1), Stat3 (a-Stat3), or Stat5 (a-Stat5a or a-Stat5b); asterisk indicates position of supershifted complexes. Data are consistent with those obtained from 4 independent experiments.

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, and other references mentioned herein are incorporated by reference in their entirety. In case of conflict, the present specification, including any definitions, will control. In addition, the materials, methods and examples given are illustrative in nature only and not intended to be limiting. Accordingly, this invention may be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

Materials and Methods

Cells and Reagents.

v-Src-transformed mouse fibroblasts (NIH3T3/v-Src), human pancreatic cancer (Panc-1) and leukemic (K562) lines have been described (14-16). The human pancreatic cancer lines, Colo-357 and Mia-PaCa-2 were kind gifts from Drs. Lancaster and Mokenge (Moffitt Cancer Center). The immortalized human pancreatic duct epithelial cell (HPDEC) line was obtained from Dr. Tsao, OCI, UHN-PMH, Toronto) (17). Except for HPDEC grown in Keratinocyte-SFM media supplemented with 0.2 ng EGF, 30 µg/mL bovine pituitary extract and containing antimycol, and K562 line in RPMI 1640 containing 10% heat-inactivated FBS and 100 units/ml penicillin-streptomycin, all other cell lines were grown in Dulbecco's modified Eagle's medium (DMEM) containing 5% iron-supplemented bovine calf serum and 100 units/ml penicillin-streptomycin. Recombinant human EGF (hEGF) is from Creative Biolabs, Port Jefferson Station, N.Y.); Gemcitabine is from Ely Lilly (Indianapolis, Ind.).

Nuclear Extract Preparation and Gel Shift Assays.

Nuclear extract preparation and DNA-binding with electrophoretic mobility shift assay (EMSA) were carried out, as previously reported (14, 15). The $^{32}$P-labeled oligonucleotide probes used were hSIE (high affinity sis-inducible element from the c-fos gene, m67 variant), 5'-AGCTTCATTTCCCG-TAAATCCCTA; (SEQ ID NO:1) that binds Stat1 and Stat3 (Wagner et al., 1990) and the MGFe (mammary gland factor element from the bovine β-casein gene promoter, 5'-AG-ATTTCTAGGAATTCAA; (SEQ ID NO:2) that binds Stat1 and Stat5 (Gouilleux et al., 1995; Seidel et al., 1995).

SDS-PAGE/Western Blot Analysis.

Western blotting analysis was performed as previously described (15, 18). Primary antibodies used were anti-Stat3 (C20) (Santa Cruz, Santa Cruz, Calif.), anti-pY845EGFR (Upstate Biotech, Millipore, Billerica, Mass.), and antibodies against pY705Stat3, Stat3, pY1068EGFR, pY1086EGFR, pY1173EGFR, EGFR, pY416Src, Src, c-Myc, and β-Actin from Cell Signaling (Danvers, Mass.).

Inhibitors

The inhibitors used herein are known to the art.

ZD or ZD1839 (Iressa™) is also referred to as Gefitinib (CAS No. 184475-32-2). ZD1839 has the molecular formula $C_{22}H_{24}ClFN_4O_3$. ZD has the formula:

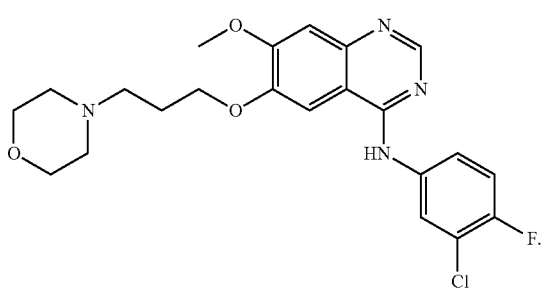 [SMILES: COc1cc2ncnc(Nc3ccc(F)c(Cl)c3)c2cc1OCCCN1CCOCC1]

See References 24 and 25.

S3I-201 or S3I is also referred to as NSC 74859 (Cas No. 501919-59-1). S3I has the molecular formula $C_{16}H_{15}NO_7S$. S3I has the formula:

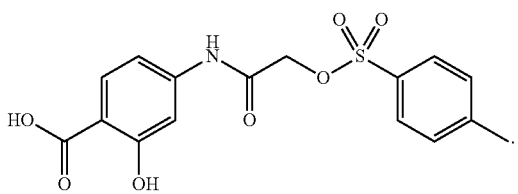 [SMILES: Cc1ccc(S(=O)(=O)OCC(=O)Nc2ccc(C(=O)O)c(O)c2)cc1]

See Reference 30.

Das or Dasatinib (Sprycel™) is also referred to as BMS-354825 (CAS No. 302962-49-8). Das has the molecular formula $C_{22}H_{26}ClN_7O_2S$. Das has the formula:

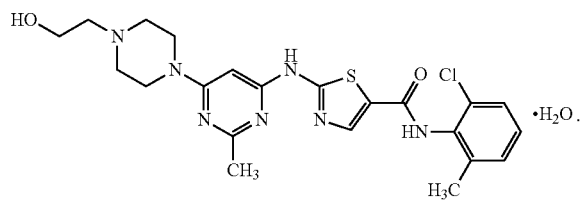

See Reference 23, 29, and 35.

AG490 is also referred to as Tyrphostin AG490 (CAS No. 133550-30-8). AG490 has the molecular formula $C_{17}H_{14}N_2O_3$. AG490 has the formula:

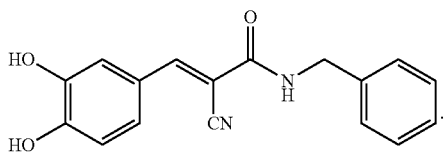 [SMILES: N#C/C(=C\c1ccc(O)c(O)c1)C(=O)NCc1ccccc1]

See Reference 14.

Small-Interfering RNA (siRNA) Transfection.

siRNA sequences for EGFR and Src were ordered from Dharmacon RNAi Technologies, Thermo Scientific (Lafayette, Colo.). Sequences used are: EGFR sense strand, 5'-GAAGGAAACUGAAUUCAAAUU-3', SEQ ID NO:3; EGFR antisense strand, 5'-UUUGAAUUCAGUUUCCUU-CUU-3', SEQ ID NO:4'; control siRNA sense strand, 5'-AGUAAUACAACGGUAAAGAUU-3', SEQ ID NO:5; and control siRNA antisense strand, 5'-UCUUUACCGUU-GUAUUACUUU-3', SEQ ID NO:6. The c-Src SMARTpool siRNA reagent (NM-005417, Catalog #M-003175-01-05) was used for Src. Transfection into cells was performed using 20 nM of EGFR siRNA or 25 nM of Src siRNA and 8 μl Lipofectamine RNAiMAX (Invitrogen Corporation, Carlsbad, Calif.) in OPTI-MEM culture medium (GIBCO, Invitrogen).

Cell Proliferation Viability Assay and Annexin V Binding and Flow Cytometry.

Proliferating cells in 6-well or 96-well plates were treated once with 0.1-1 mM ZD1839 (Iressa) (reference 25), 100 nM Dasatinib (references 23 and 35), 50-100 μM S31-201, 1 μM Gemcitabine (reference 43), or combinations of inhibitors for up to 96 h. Viable cells were counted by trypan blue exclusion/phase contrast microscopy or assessed by CyQuant cell viability assay, according to manufacturer's (Invitrogen) instructions, or cells were processed for Annexin V binding (BD Biosciences) with flow cytometry for apoptosis. S31-201 is fully described in reference 30 (see below).

Colony Survival Assay.

Single-cell suspension of Panc-1 and Colo-357 cells were seeded in 6-cm dishes (500 cells per well) and assayed as previously reported (19), treated the next day with inhibitors for 48 h, and allowed to grow until large colonies were visible. Colonies were stained with crystal violet for 4 h and counted under phase-contrast microscope.

Cell Migration and Matrigel Invasion Assays.

Cell migration and invasion experiments were carried out and quantified as previously described (20), using Bio-Coat migration chambers (Becton Dickinson, Franklin, N.J.) of 24-well companion plates with cell culture inserts containing 8 μm pore size filters, according to the manufacturer's protocol.

Statistical Analysis.

Statistical analysis was performed on mean values using Prism GraphPad Software, Inc. (La Jolla, Calif.). The significance of differences between groups was determined by paired t-test at $p < 0.05^*$, $< 0.01^{}$, and $< 0.001^{*}$.

Results

Aberrant EGFR, Src and Stat3 in Pancreatic Cancer Lines.

Consistent with published reports (6, 7), Stat3 activity, per DNA-binding with EMSA analysis in nuclear extract preparations is constitutive in Panc-1 and Colo-357, low in Mia-Paca-2, and undetectable in the normal human pancreatic duct epithelial cells (HPDEC), compared to aberrant levels in NIH3T3/v-Src (15) (FIG. 1A(i)). Per supershift analysis, the DNA-protein complex contains Stat3 (FIG. 1A(i), lane 3). By contrasts, Stat5 activity is undetectable in pancreatic cancer cells (FIG. 1A(ii)), compared to aberrant levels in the K562 leukemic cells (16).

EGFR and c-Src are aberrant in many human cancers (2, 4). Immunoblotting analysis showed a moderate pY416c-Src level in Mia-Paca-2, but enhanced levels in Panc-1 and Colo-357 cells similar to levels in NIH3T3/v-Src, compared to low levels in HPDEC (FIG. 1B(i), upper panel). The elevated pY416Src levels parallel enhanced levels of the Src-sensitive pY845EGFR motif (21) in Panc-1 and Colo-357 cells, compared to low levels of same in HPDEC (FIG. 1B(i), lower panel). Total Src or EGFR protein remained unchanged. Immunoblotting analysis further showed elevated levels of the EGFR autophosphorylation motifs (22), pY1068EGFR (FIG. 1C(i), lanes 2 and 7), pY1086EGFR (FIG. 1C(ii), lanes 2 and 7) and pY1173EGFR (FIG. 1C(iii), lanes 2 and 7) in Panc-1 and Colo-357, compared to basal levels of same in HPDEC (FIG. 1C(i)-(iii), lane 1).

Functional Integration of EGFR and Src in Pancreatic Cancer Cells.

We next examined the functional relationship between the activated EGFR and Src. Immunoblotting analysis showed treatment of cells with Dasatinib (Das) inhibited Src activity (pY416Src) (23) and induced an early (1 h) and a sustained (24 h) decrease in pY845EGFR levels (FIG. 1B(ii)). By contrast, no detectable changes in pY416Src and pY845EGFR levels were induced by treatment with the pan-ErbB inhibitor, PD169540 (PD169) (24) (data not shown) or the selective EGFR inhibitor, ZD 1839 (ZD, Iressa) (25) (FIG. 1B(ii)). In confirmation, siRNA knockdown of c-Src abrogated pY845EGFR levels (FIG. 1B(iii), Src siRNA), while EGFR knockdown by siRNA had minimal effect on pY416Src level (FIG. 1B(iv), EGFR siRNA). Scrambled siRNA has no effect (FIG. 1B(iii) and (iv), con siRNA). Thus, elevated pY845EGFR levels in pancreatic cancer cells are sensitive to Src activity.

Immunoblotting analysis further showed that treatment of Panc-1 and Colo-357 cells with ZD diminished pY1173EGFR levels (FIG. 1C(iii), lanes 3, 4, 8 and 9) by as early as 1 h and up to 24 h, with no effect on pY1068EGFR (/FIG. 1C(i), lanes 3, 4, 8 and 9) or pY1086EGFR level (FIG. 1C(ii), lanes 3, 4, 8 and 9), suggesting that EGFR kinase is essential for the induction of pY1173EGFR levels, but not pY1068EGFR or pY1086EGFR. By contrast, Das treatment decreased pY1068EGFR and pY1086EGFR levels (FIG. 1C(i) and (ii), lanes 5, 6, 10 and 11), with minimal effect on pYEGFR1173 (FIG. 1C(iii), lanes 5, 6, 10 and 11).

Both EGFR and Src Promote Aberrant Stat3 Activation.

Figure 2:
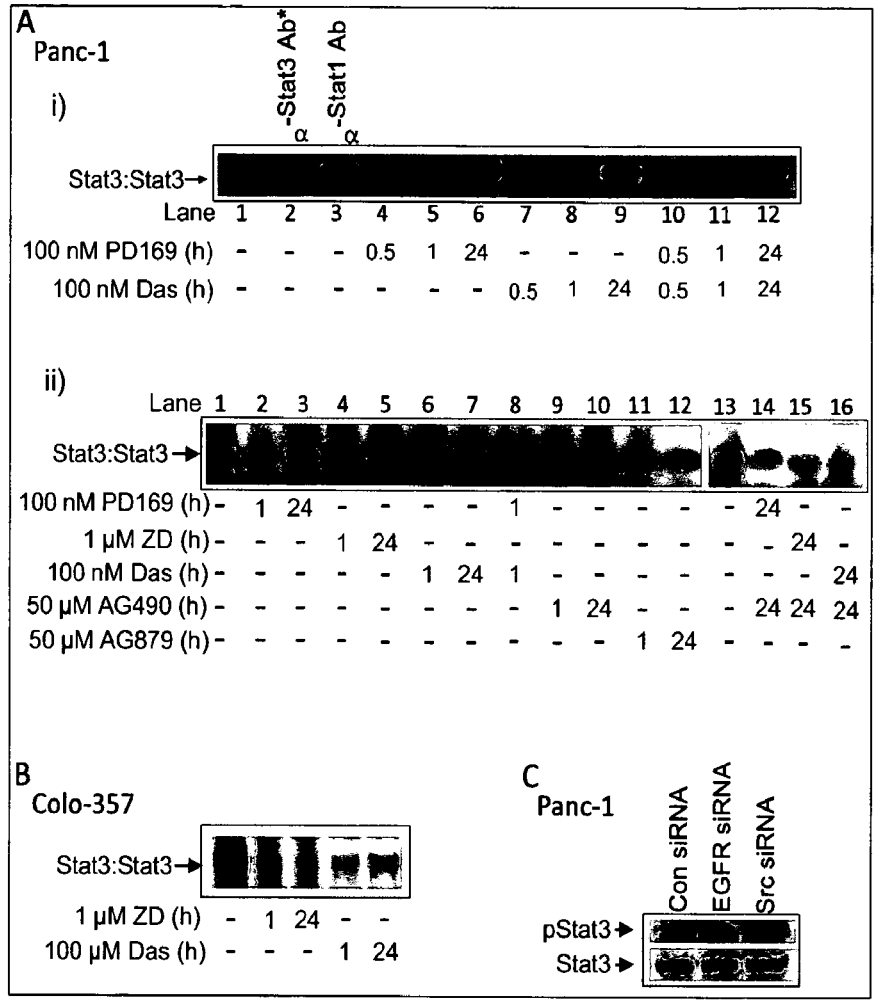
FIG. 2 depicts EMSA and immunoblotting analyses for effects of inhibitors on Stat3. (A and B) EMSA analysis of Stat3 DNA-binding activity in (A) Panc-1 or (B) Colo-357 cells treated or untreated with the pan ErbB inhibitor, PD169540 (PD169), ZD 1839 (ZD), Dasatinib (Das), the Jak inhibitor, AG490, the ErbB2-selective inhibitor, AG879, or inhibitor combinations for the indicated times, or (C) immunoblotting analysis of whole-cell lysates from Panc-1 cells transfected with EGFR siRNA, Src siRNA, or scrambled siRNA (control) and probing for pStat3 or Stat3. *Supershift analysis. Data are consistent with those obtained from 3 independent experiments.

Both the pY1068EGFR and pY1086EGFR levels are binding sites for Stat3 (27, 28). Given the concurrent EGFR and Src activation in Panc-1 and Colo-357 cells, we sought to define the regulation of aberrant Stat3 activation. By in vitro DNA-binding assay with EMSA analysis of nuclear extract preparations, we observe an early repression (in the first 30 min to 1 h of treatment) of constitutively-active Stat3 by the pan-ErbB inhibitor, PD169540 (PD169), the ErbB2-selective inhibitor, AG879 (7), ZD, or Das (FIG. 2A(i), lanes 4, 5, 7, and 8, and (ii), lanes 2, 4, 6, and 11, and FIG. 2B, 1 h), or by a combined PD169 and Das (FIG. 2A(i), lanes 10 and 11, and (ii), lane 8). However, the Stat3 activity in Panc-1 cells consistently rebounded following 24 h treatments with Das, ZD, or PD169 (FIGS. 2A(i) and (ii), 24 h), even though EGFR or Src activity remained inhibited (FIGS. 1B and 1C, 24 h). Twenty-four hour treatment with the AG879 moderately inhibited Stat3 activity (FIG. 2A(ii), lane 12), which we speculate may be due to its widespread activity as a pan-ErbB inhibitor. By contrast, treatment with the Jak inhibitor, AG490 for 1 h had no effect on constitutive Stat3 activity, but surprisingly abolished Stat3 activity at 24 h treatment (FIG. 2A(ii), lanes 9 and 10). Moreover, combined treatment with AG490 and ZD, Das or PD169 for 24 h similarly abolished constitutively-active Stat3 (FIG. 2A(ii), lanes 14, 15, and 16). In Colo-357, Stat3 activity was inhibited by both ZD and Das, with the effects more striking for Dasatinib (FIG. 2B). These findings together reveal a pattern of constitutive Stat3 activation in pancreatic cancer cells that is mediated by both EGFR and Src, and a compensatory, Jak-dependent secondary Stat3 activity. A similar pattern of Stat3 activation has been observed in head and neck squamous carcinoma, mesothelioma, squamous cell skin carcinoma, and non-small cell lung cancer cell lines following the inhibition of Src (29). In further support, the siRNA knockdown of EGFR (EGFR siRNA) or Src (Src siRNA) led to pStat3 suppression, as assayed by immunoblotting analysis (FIG. 2C). Scrambled siRNA (con) has no effect. Immunoblotting analysis also shows that EGF stimulation induces pY705Stat3, pY1086EGFR, pY1173EGFR, pY845EGFR and pY416c-Src (Supplemental FIG. S1(i)-(iii), lane 4) over and above constitutive levels in Panc-1 cells, in a manner that is similar to the induction of same in response to the stimulation of normal HPDEC (Supplemental FIG. S1, lane 2), except for pY1068EGFR levels in Panc-1 (FIG. S1(ii), upper right panel). In control studies, immunoblotting analysis showed elevated pErk1/ pErk2MAPK and pAkt in Panc-1 and Colo-357 cells compared to normal HPDEC, neither of which was significantly affected by treatment with ZD or Das (data not shown).

Inhibition of Stat3 Sensitizes Pancreatic Cancer Cells In Vitro to EGFR and Src Inhibitors.

Given the preceding data on the inter-relation between EGFR, Src and Stat3 activation, we investigated the biological implications and the therapeutic potential of a combinatorial approach. Dasatinib and ZD were used at 100 nM and 0.1-1 µM, respectively, as in literature reports (23, 24), while the Stat3 inhibitor, S3I-201 was used at the sub-optimum, 50 µM, or at the 100 µM required to inhibit Stat3 activation (30). Viable cell count by trypan blue exclusion/phase-contrast microscopy showed that treatment with 1 µM ZD, 100 nM Das, or 50 µM S3I-201 alone minimally affected cell viability by 24 h (FIG. 3A Day 1). By contrast, treatment for 48 to 96 h with or Das or S3I-201 alone progressively decreased cell viability, while treatment for the same period with ZD showed minimal effect (FIG. 3A), except at 96 h when the number of viable Panc-1 cells decreased (FIG. 3A(i), ZD, Day 4). Comparatively, the combined inhibition of Stat3 (by S3I-201) and EGFR (by ZD) or Src (by Das) or the combined treatment with AG490 (Jaks inhibitor) and ZD or Das induced greater losses of viability at 48-96 h (FIGS. 3A and B). The effects on cell viability as captured by trypan blue exclusion were confirmed by the CyQuant cell proliferation/viability assay. Unlike 24 h treatment duration that showed minimal effect on viability (FIG. 3A), CyQuant assay showed that 48-h treatment with each inhibitor alone decreased viable cell numbers (quantified as fluorescent unit, FU) in a dose-dependent manner (FIG. 3C, ZD, Das and S3I-201). We infer from the graphs that treatment with 1 µM ZD for 48 h has minimal effect on cell viability (FIGS. 3C(i) and (iv)), as observed by the trypan blue exclusion assay (FIG. 3A). However, the observed effects of single agents were significantly weaker compared to the concurrent treatment with a Stat3 inhibitor and an inhibitor of EGFR or Src. Results show that the treatment with S3I-201 increased the sensitivity of Panc-1 and Colo-357 cells to ZD and Das, shifting the dose-response curves to the left (FIG. 3C, ZD+S3I-201, and Das+S3I-201). Concurrent treatment with S3I-201 significantly decreased the IC50 values as follows: 17 to 0.4 µM, and 100 to 6 nM, respectively, for ZD and Das against Panc-1 viability (FIG. 3C(i) and (ii)); and 6.5 to 2.4 µM, and 90 to 8 nM, respectively for ZD and Das against Colo-357 viability (FIGS. 3C(iv) and (v)). For the impact of ZD and Das on the sensitivity to S3I-201, CyQuant cell viability assay showed that Das, but not ZD increased the sensitivity of both cell lines to S3I-201, decreasing its IC50 from 40 to 15 µM, and from 45 to 20 µM, respectively, for effects on Panc-1 and Colo-357 cells (FIGS. 3C(iii) and (iv)). Thus, treatment with S3I-201 sensitized cells to ZD and Das, while treatment with Das, but not ZD similarly sensitized cells to S3I-201.

Given the clinical implications of these findings, we extended these studies to examine the effect of EGFR Src and Stat3 pathway on the response to Gemcitabine, the anti-metabolite agent used in the treatment of pancreatic cancer. CyQuant cell proliferation/viability studies showed that inhibition of EGFR, Src or Stat3 sensitized Panc-1 and Colo-357 cells to Gemcitabine (FIG. 3D). More importantly, the combined inhibition of Stat3 and EGFR or Src induced a higher sensitization of cells to Gemcitabine than that induced by the inhibition of any one alone (FIG. 3D).

As known to the skilled, Gemcitabine is a nucleoside analog of cytidine which interferes with DNA replication, arresting tumor growth and resulting in apoptosis of the cell. Gemcitabine is also known to bind to the active site of the enzyme ribonucleotide reductase (RNR) to irreversibly inactive the enzyme, thus interfering with the cell's ability to produce deoxyribonucleotides necessary for DNA replication and repair. This also leads to apoptosis. As noted above, the combined inhibition of Stat3 and EGFR or Src induces a higher sensitization of cells to Gemcitabine, creating another possibility for combination therapy of tumors.

Figure 3:
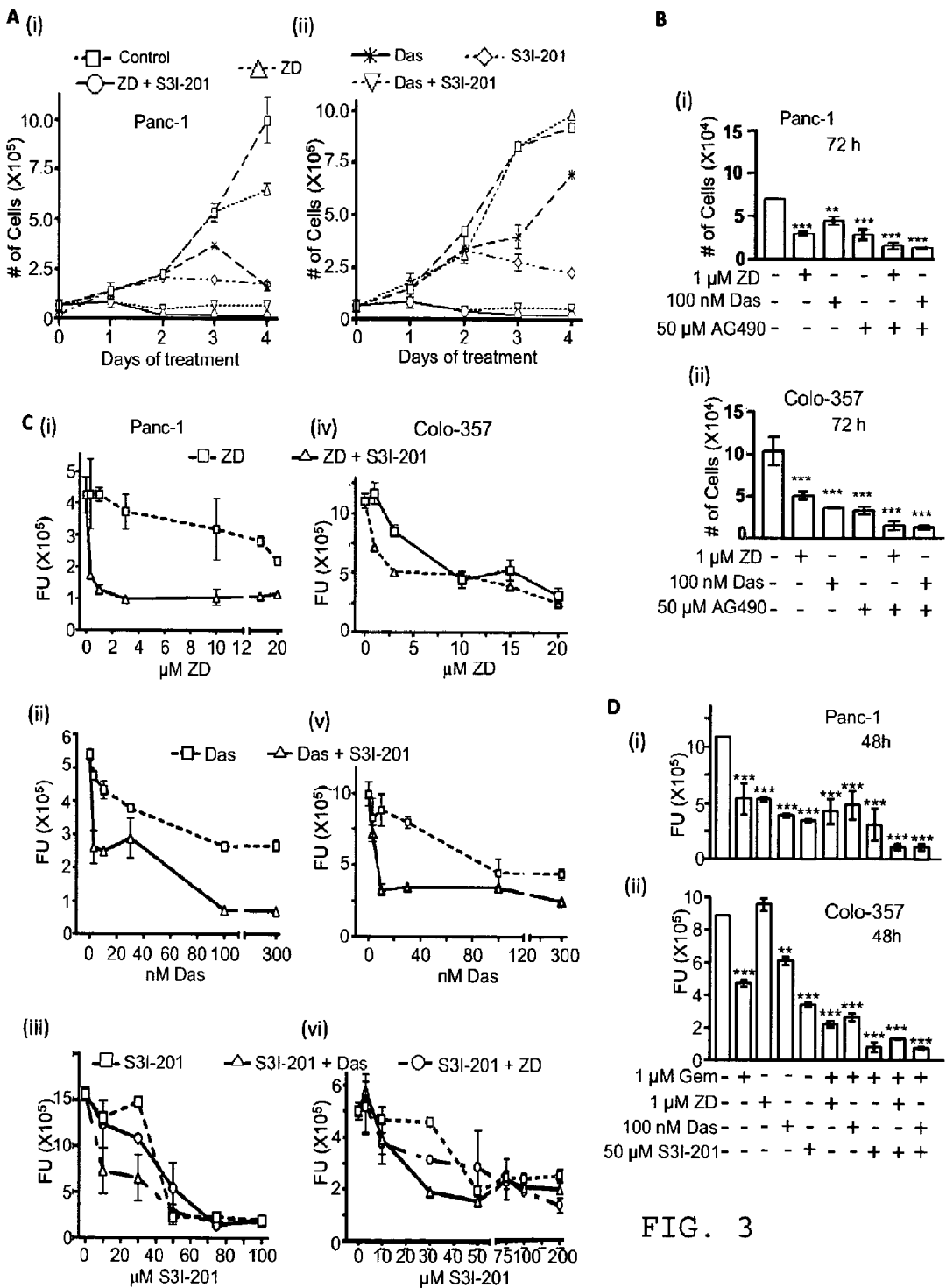
FIG. 3 presents data of cell viability studies for effects of inhibitors. (A and B) Trypan blue exclusion/phase-contrast microscopy for viable Panc-1 or Colo-357 cells following treatment for 0-96-h inhibitor with 1 µM ZD, 100 nM Das, 50 µM S3I-201, Jak inhibitor, AG490, or combinations; (C and D) CyQuant cell proliferation assay for viability of Panc-1 (C, left panel, and D(i)) or Colo-357 cells (C, right panel and D(ii)) for effects of 48-h treatments with the designated concentrations of ZD, Das, S3I-201, Gemcitabine (Gem) alone and in combinations. Values, mean and S.D., n=4 experiments each in triplicates. p values, *–<0.05, –<0.01, and *–<0.001.
Figure 4:
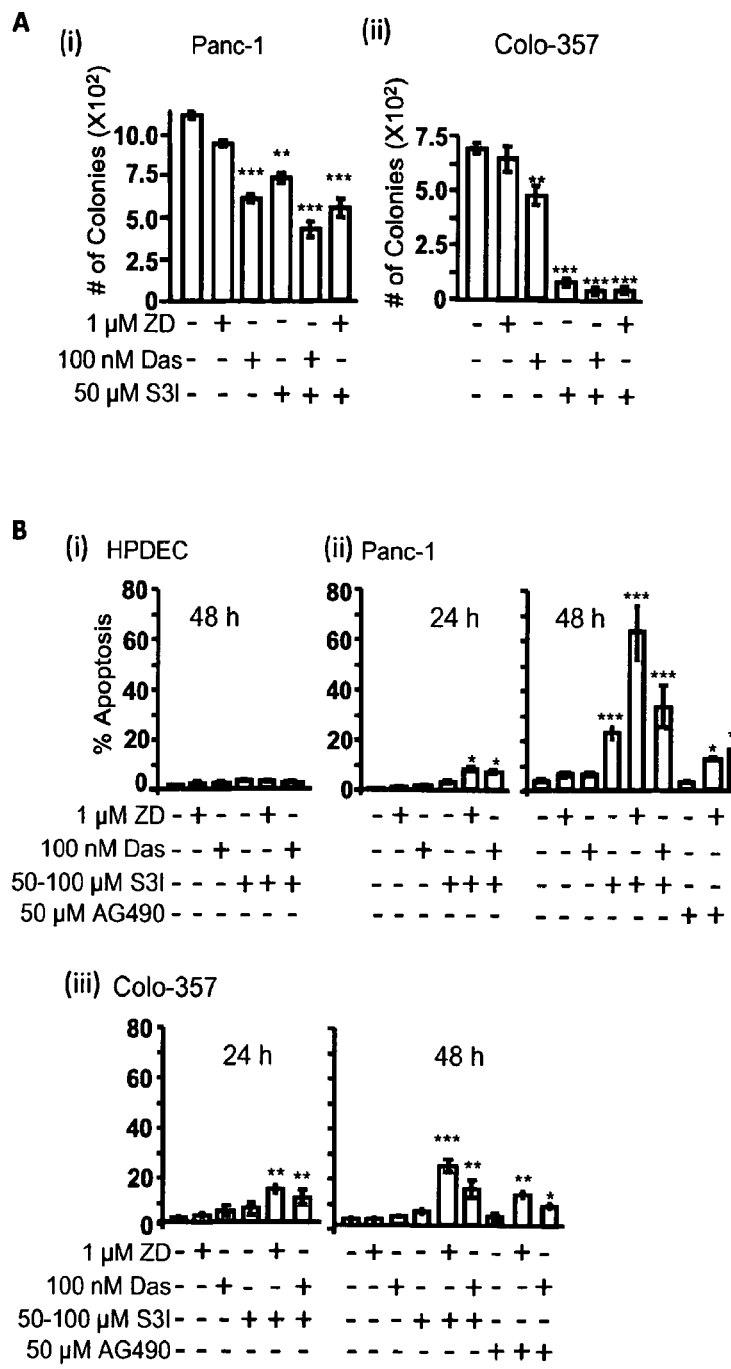
FIG. 4 shows colony survival and apoptosis studies for effects of inhibitors. (A) Number of colonies emerging from cells in culture (500 per 6 cm dish) untreated or treated once with ZD1839 (ZD), Dasatinib (Das), S3I-201 (S3I), or combinations and allowed to culture; or (B) Annexin V binding/Flow Cytometry analysis of normal HPDEC, Panc-1 or Colo-357 cells treated or untreated with inhibitors or combinations. Values, mean and S.D., n=4 experiments each in triplicates. p values, *–<0.05, –<0.01, and *–<0.001.

To further explore the sensitization potential of inhibition of aberrant Stat3, we performed colony survival assay (19). Results show that inhibition of Src (by Das) or Stat3 (by S3I-201 (S3I)), but not EGFR inhibition (by ZD) resulted in reduced colony numbers (FIG. 4A). More importantly, the concurrent inhibition of Stat3 and EGFR or Src resulted in much lower colony numbers (FIG. 4A), consistent with the much greater loss of viable cells due to the combined inhibition of Stat3 and EGFR or Src (FIG. 3). To extend these studies, we performed Annexin V binding/Flow Cytometric analysis for apoptosis. Higher percentages of Panc-1 and Colo-357 cells undergoing apoptosis were observed for concurrent inhibition of Stat3 and EGFR or Src than for the inhibition any one signaling molecule alone (FIG. 4B(ii) and (iii)). Similar results were obtained for the concurrent treatments with AG490 and ZD or Das (FIG. 4B(ii) and (iii)). By contrast, similar treatments of normal HPDECs showed no significant apoptosis (FIG. 4B(i)) with the combination treatments. Thus, we establish that pancreatic cancer cells have higher sensitivity to concurrent inhibition of Stat3 and EGFR or Src than to the inhibition of a single entity.

EGFR, Src and Stat3 Together Promote Pancreatic Cancer Cell Migration and Invasion.

Figure 5:
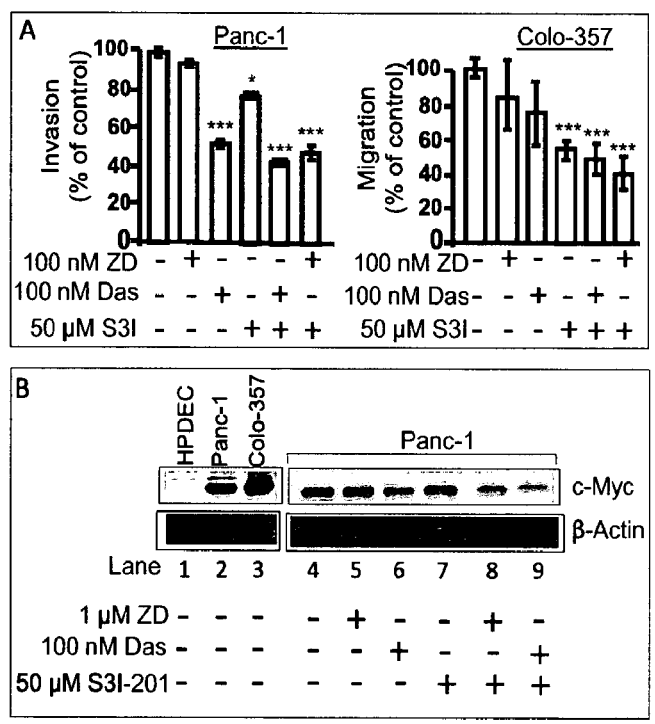
FIG. 5 presents the concurrent inhibition of Stat3 and EGFR or Src inhibits migration and invasion and suppresses c-Myc expression. (A) Effects of ZD1839 (ZD), Dasatinib (Das), and/or S3I-201 (S3I) on migration and invasion; (B) Immunoblotting analysis of whole-cell lysates for c-Myc and b-Actin expression in Panc-1 cells. Values, mean and S.D., n=3-4 experiments each in triplicates. p values, *–<0.05, –<0.01, and *–<0.001.

Aberrantly-active Src and Stat3 have both been implicated in tumor cell motility, migration, invasion and metastasis (4, 23). in vitro matrigel assay confirmed that inhibition of Src or Stat3 alone suppresses migration and invasion (FIG. 5A). However, concurrent inhibition of Stat3 and EGFR or Src for 24-h has a stronger effect on Colo-357 migration and Panc-1 invasion, except for Src inhibition, which showed a similar effect on Panc-1 migration (FIG. 5A). At the 24-h treatment when these studies were done, there is no significant effect on cell viability (FIG. 3). These findings are further evidence that pancreatic cancer lines are more sensitive to concurrent inhibition of Stat3 and Src or EGFR.

EGFR, Src and Stat3 Module Regulates c-Myc Over-Expression in Pancreatic Cancer Cells.

For insight into the underlying molecular mechanisms by which the EGFR, Src and Stat3 pathway may support the cancer phenotype, we studied the regulation of key cancer-relevant genes. We show that c-Myc is over-expressed in pancreatic cancer lines compared to normal HPDEC (FIG. 5B). Furthermore, the concurrent inhibition of Stat3 and EGFR or Src consistently repressed c-Myc expression. These findings suggest a functional synergy between EGFR, Src and Stat3 in inducing c-Myc expression in the context of pancreatic cancer phenotype and that the stronger repression of c-Myc expression contributes to the antitumor cell effects of and the increased sensitivity of pancreatic cancer lines to concurrent Stat3 and EGFR or Src inhibition.

Inhibition of Tumor Growth by Combination Treatment

Figure 6:
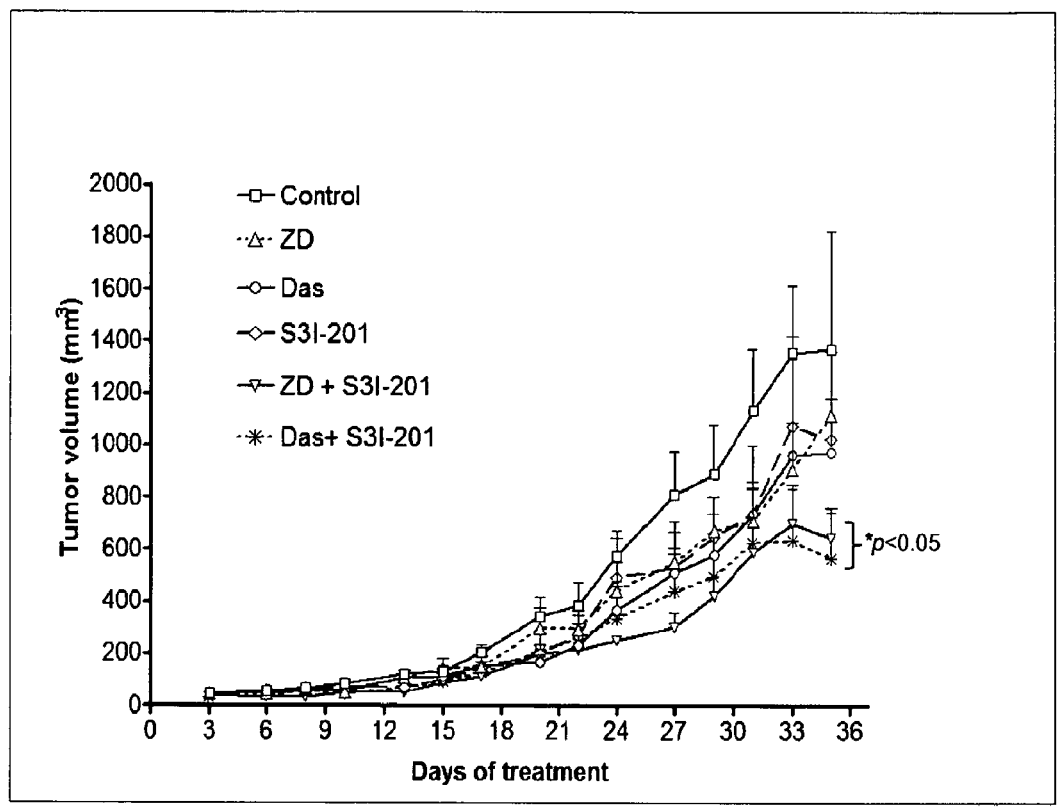
FIG. 6 is a line graph showing progression of tumor volume under the different therapies; concurrent inhibition of Stat3 and EGFR or Src induces human pancreatic tumor growth inhibition in xenografts.

Concurrent inhibition of Stat3 and EGFR or Src induces human pancreatic tumor growth inhibition in xenografts. Subcutaneous xenografts of Colo-357, a metastatic pancreatic adenocarcinoma line were used to study the therapeutic implication of the Stat3, EGFR and Src inter-relationships and to evaluate the in vivo antitumor effects of concurrent inhibition of Stat3 and EGFR or Src. Data showed that in general, xenografts of Colo-357 cells showed low responsiveness to treatment with inhibitor of EGFR, Src or Stat3 alone, although, as the therapy progressed, those tumors treated with only one inhibitor alone appeared to show reduced growth, which was statistically not significant from the control, non-treated tumors (FIG. 6). By contrast, tumors from mice treated with combined S3I-201 and Das or S3I-201 and ZD consistently showed reduced growth and smaller tumor sizes throughout the entire study (FIG. 6). Thus, the residual tumor volumes (sizes) for tumors in mice treated with combination inhibitors were significantly different ($p<0.05$) from tumor volumes for tumors in control mice at days 20 and upwards post treatment. These in vivo antitumor effects of combination treatment with inhibitors of S3I-201 and Das or S3I-201 and ZD are consistent with the in vitro antitumor cell data and together indicate that aberrant Stat3 cooperates with hyperactive EGFR or Src to sustain human pancreatic cancer.

Discussion

Within the context of aberrations in the EGFR, Src and Stat3 pathway in pancreatic cancer, present study reveals a strong role for Src in supporting aberrant EGFR activation by not only inducing the phosphorylation of Y845EGFR motif (31), but also promoting the induction of pY1068EGFR and pY1086EGFR motifs. These Src-promoted events will greatly influence the status of EGFR in pancreatic cancer cells. A role for EGFR in aberrant Stat3 activation in cancer cells has previously been reported in other tumor cells, including head and neck squamous cell carcinoma and breast cancer (26, 32). Present study extends those findings to pancreatic cancer and show that EGFR is key in facilitating aberrant Stat3 activation. Moreover, the pY1068EGFR and pY1086EGFR induction by Src is likely to have significant impact on the activation of Stat3, given that these two motifs are essential sites for the binding of Stat3 to EGFR in order to promote its phosphorylation and activation (27, 28). Furthermore, Src may not only facilitate Stat3 activation via the induction of those two Tyr motifs of EGFR, but it can also directly phosphorylate Stat3, as has been previously reported in other systems (18). It is therefore consistent that both hyperactive EGFR and Src promote baseline constitutive Stat3 activation in pancreatic cancer, as revealed by our study.

The present study is also in agreement with an earlier report of ErbB-2-dependent constitutive Stat3 activation in Mia-Paca-2 and UK Pan-1 cells (7) and another study that showed that the full induction of Stat3 activation by ErbB2 required both Src and Jaks (33). Our findings indicate that Jaks contribute to the maintenance of constitutive activation in revealing a Jak-dependent compensatory mechanism of Stat3 activation upon inhibition of EGFR and Src. Given that Jaks inhibition did not abolish aberrant Stat3 at the earliest time point, we deduce that this family of cytoplasmic tyrosine kinases may not be the predominant mediators of the baseline aberrant Stat3. Thus, in pancreatic cancer cells, a two-phase model of activation of Stat3 signaling emerges composed of an EGFR- and Src-dependent baseline, constitutive Stat3 induction, and an induced Stat3 activation that is dependent on Jaks. The observed secondary induction of Stat3 activation via Jaks has similarly been reported in head and neck squamous cell carcinoma line (29) and could be due to growth-stimulatory factors released from tumor cells (34), which in turn would induce the activation of Jaks and thereby promote Stat3 activation.

EGFR, Src and Stat3 has each independently been established to have critical roles in malignant transformation (6, 14, 23, 26, 35), while their collective roles in promoting tumorigenesis have not been explored. While the inhibition of the activity of each of the three proteins induced antitumor cell response to some degree, data presented here strongly indicate that the multiple targeting of Stat3 and EGFR or Src together has a higher potential to inhibit growth, viability, survival, malignant transformation, and migration and invasion in vitro.

Significantly, hyperactivation of the EGFR signaling has been deemed a prognostic indicator of low survival among pancreatic cancer patients (36-38). Also, there is evidence to indicate that the concurrence with aberrant Src signaling potentiates the effects of aberrant EGFR and induces biological synergy (3, 21, 39). Given the potential collective roles of Stat3, EGFR and Src in promoting and supporting pancreatic cancer, the inhibition of any single entity alone is unlikely to be insufficient to impact the disease. Present data that simultaneous inhibition of Stat3 and EGFR or Src induced greater antitumor cell effects and a higher sensitization to Gemcitabine provides a strong support for the opinion that Stat3 may cooperate with EGFR and Src to support the malignant phenotype. Indeed, the inhibition of Stat3 seemed to sensitize pancreatic cancer cells to the antitumor cell effects of ZD and Das. Multiple targeting of Stat3 and EGFR or Src therefore has the potential to induce a greater antitumor efficacy. This is supported by our present data that concurrent treatment with theStat3 inhibitor, S3I-201 and ZD or Das induced greater regression of xenografts of Colo-357 than treatment with either inhibitor alone. Such a multiple-targeted therapy has received a strong interest in recent times, particularly given the dismal results in certain cases of molecular targeted monotherapy, such as anti-EGFR monotherapy (40, 41). Thus, a combined Gemcitabine and Erlotinib (EGFR TK inhibitor) therapy has recently been approved for patients with locally advanced/metastatic pancreatic cancer (42, 43), although we note by our data that the inhibition of Stat3 and EGFR or Src together induces a higher Gemcitabine sensitivity than inhibition of EGFR alone. The enhanced antitumor effects due combined Stat3 and EGFR or Src inhibitors may in part be due stronger repression of the expression of c-Myc oncogene. Altogether, present study provides support for a multiple-modality therapeutic approach and lays the foundation for concurrent targeting of aberrant Stat3 and EGFR or Src as a more effective approach for achieving an enhanced antitumor therapeutic efficacy in pancreatic cancer.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

References

1. Tzeng C W, Frolov A, Frolova N, et al. EGFR genomic gain and aberrant pathway signaling in pancreatic cancer patients. J Surg Res 2007; 143:20-6.
2. Korc M, Meltzer P, Trent J. Enhanced expression of epidermal growth factor receptor correlates with alterations of chromosome 7 in human pancreatic cancer. Proc Natl Acad Sci USA 1986; 83:5141-4.
3. Lutz M P, Esser I B, Flossmann-Kast B B M, et al. Overexpression and Activation of the Tyrosine Kinase Src in Human Pancreatic Carcinoma. Biochem Biophys Res Commun 1998; 243::503-8.
4. Trevion J G, Summy J M, Lesslie D P, et al. Inhibition of SRC expression and activity inhibits tumor progression and metastasis of human pancreatic adenocarcinoma cells in an orthotopic nude mouse model. Am J Pathol 2006; 168:962-72.
5. Parsons J T, Parsons S J. Src family protein tyrosine kinases: cooperating with growth factor and adhesion signaling pathways. Curr Opin Cell Biol 1997; 9:187-92.
6. Scholz A S H, Detjen K M, Peters M, et al. Activated signal transducer and activator of transcription 3 (STAT3) supports the malignant phenotype of human pancreatic cancer. Gastroenterology 2003; 125:891-905.
7. DeArmond D, Brattain M G, Jessup J M, et al. Autocrine-mediated ErbB-2 kinase activation of STAT3 is required for growth factor independence of pancreatic cancer cell lines. Oncogene 2003; 22:7781-95.
8. Trevino J G, Gray M J, Nawrocki S T, et al. Src activation of Stat3 is an independent requirement from NF-kappaB activation for constitutive IL-8 expression in human pancreatic adenocarcinoma cells. Angiogenesis 2006; 9:101-10.
9. Toyonaga T, Nakano K, Nagano M, et al. Blockade of constitutively activated Janus kinase/signal transducer and activator of transcription-3 pathway inhibits growth of human pancreatic cancer. Cancer Lett 2003; 201:107-16.
10. Darnell J E. Validating Stat3 in cancer therapy. Nat Med 2005; 11:595-6.
11. Yu H, Jove R. The STATS of Cancer-New molecular targets come of age. Nat Rev Cancer 2004; 4:97-105.
12. Turkson J. STAT proteins as novel targets for cancer drug discovery. Expert Opin Ther Targets 2004; 8:409-22.
13. Yue P, Turkson J. Targeting STAT3 in cancer: how successful are we? Expert Opin Investig Drugs 2009; 18:45-56.
14. Garcia R, Bowman T L, Niu G, et al. Constitutive activation of Stat3 by the Src and JAK tyrosine kinases participates in growth regulation of human breast carcinoma cells. Oncogene 2001; 20:2499-513.
15. Turkson J, Bowman T, Garcia R, Caldenhoven E, De Groot R P, Jove R. Stat3 activation by Src induces specific gene regulation and is required for cell transformation. Mol Cell Biol 1998; 18:2545-52.
16. Huang M, Dorsey J F, Epling-Burnette P K, et al. Inhibition of Bcr-Abl kinase activity by PD180970 blocks constitutive activation of Stat5 and growth of CML cells. Oncogene 2002; 21:8804-16.
17. Ouyang H, Mou L J, Luk C, et al. Immortal human pancreatic duct epithelial cell lines with near normal genotype and phenotype. Am J Pathol 2000; 157:1623-31.
18. Zhang Y, Turkson J, Carter-Su C, et al. Activation of Stat3 in v-Src Transformed Fibroblasts Requires Cooperation of Jak1 Kinase Activity. J Biol Chem 2000; 275:24935-44.
19. Zhao S, Venkatasubbarao K, Lazor J W, et al. Inhibition of STAT3Tyr705 Phosphorylation by Smad4 Suppresses Transforming Growth Factor b-Mediated Invasion and Metastasis in Pancreatic Cancer Cells. Cancer Res 2008; 68:4221-8.
20. Siddiquee K A Z, Gunning P T, Glenn M, et al. An Oxazole-Based Small-Molecule Stat3 Inhibitor Modulates Stat3 Stability and Processing and Induces Antitumor Cell Effects. ACS Chem Biol 2007; 2:787-98.
21. Tice D A, Biscardi J S, Nickles A L, Parsons S J. Mechanism of biological synergy between cellular Src and epidermal growth factor receptor. Proc Natl Acad Sci USA 1999; 96:1415-20.

22. Downward J, Parker P, Waterfield M D. Autophosphorylation sites on the epidermal growth factor receptor. Nature 1984; 311 483-5.
23. Nam S, Kim D, Cheng J Q, et al. Action of the Src family kinase inhibitor, dasatinib (BMS-354825), on human prostate cancer cells. Cancer Res 2005; 65:9185-9.
24. Mahtouk K, Hose D, Rème T, et al. Expression of EGF-family receptors and amphiregulin in multiple myeloma. Amphiregulin is a growth factor for myeloma cells. Oncogene 2005; 24:3512-24.
25. Wakeling A E, Guy S P, Woodburn J R, et al. ZD1839 (Iressa): an orally active inhibitor of epidermal growth factor signaling with potential for cancer therapy. Cancer Res 2002; 62:5749-54.
26. Song J I, Grandis J R. STAT signaling in head and neck cancer. Oncogene 2000; 19:2489-95.
27. Coffer P J, Kruijer W. EGF receptor deletions define a region specifically mediating STAT transcription factor activation. Biochem Biophys Res Commun 1995; 210:74-81.
28. Shao H, Cheng H Y, Cook R G, Tweardy D T. Identification and Characterization of Signal Transducer and Activator of Transcription 3 Recruitment Sites within the Epidermal Growth Factor Receptor. Cancer Res 2003; 63:3923-30.
29. Johnson F M, Saigal B, Tran H, Donato N J. Abrogation of signal transducer and activator of transcription 3 reactivation after Src kinase inhibition results in synergistic antitumor effects. Clin Cancer Res 2007; 13:4233-44.
30. Siddiquee K, Zhang S, Guida W C, et al. Selective chemical probe inhibitor of Stat3, identified through structure-based virtual screening, induces antitumor activity. Proc Natl Acad Sci USA 2007; 104:7391-6.
31. Biscardi J S, Maa M C, Tice D A, Cox M E, Leu T H, Parsons S J. c-Src-mediated phosphorylation of the epidermal growth factor receptor on Tyr845 and Tyr1101 is associated with modulation of receptor function. J Biol Chem 1999; 274:8335-43.
32. Sartor C I, Dziubinski M L, Yu C L, Jove R, Ethier S P. Role of epidermal growth factor receptor and STAT-3 activation in autonomous proliferation of SUM-102PT human breast cancer cells. Cancer Res 1997; 57:978-87.
33. Ren Z, Schaefer T S. ErbB-2 activates Stat3alpha in a Src- and JAK2-dependent manner. J Biol Chem 2002; 8:38486-93.
34. Salomon D S, Brandt R, Ciardiello F, Normanno N. Epidermal growth factor-related peptides and their receptors in human malignancies. Crit Rev Oncol Hematol 1995; 19:183-232.
35. Song L, Morris M, Bagui T, Lee F Y, Jove R, Haura E B. Dasatinib (BMS-354825) selectively induces apoptosis in lung cancer cells dependent on epidermal growth factor receptor signaling for survival. Cancer Res 2006 66:5542-8.
36. Uegaki K, Nio Y, Inoue Y, et al. Clinicopathological significance of epidermal growth factor and its receptor in human pancreatic cancer. Anticancer Res 1997; 17(5B):3841-7.
37. Dong M, Nio Y, Guo K J, Tamura K, Tian Y L, Dong Y T. Epidermal growth factor and its receptor as prognostic indicators in Chinese patients with pancreatic cancer. Anticancer Res 1998; 18(6B):4613-9.
38. Ueda S, Ogata S, Tsuda H, et al. The correlation between cytoplasmic overexpression of epidermal growth factor receptor and tumor aggressiveness: poor prognosis in patients with pancreatic ductal adenocarcinoma. Pancreas 2004; 29:e1-8.
39. Maa M C, Leu T H, McCarley D J, Schatzman R C, Parsons S J. Potentiation of epidermal growth factor receptor-mediated oncogenesis by c-Src: implications for the etiology of multiple human cancers. Proc Natl Acad Sci USA 1995; 92:6981-5.
40. Saif M W. Erlotinib: the first biologic in the management of pancreatic cancer. Expert Opin Pharmacother 2008; 9:1595-607.
41. Philip P A. Targeted therapies for pancreatic cancer. Gastrointest Cancer Res 2008; 2(Suppl 2):S16-59.
42. Burris H r, Rocha-Lima C. New therapeutic directions for advanced pancreatic cancer: targeting the epidermal growth factor and vascular endothelial growth factor pathways. Oncologist 2008; 13:289-98.
43. Senderowicz A M, Johnson J R, Sridhara R, Zimmerman P, Justice R, Pazdur R. Erlotinib/gemcitabine for first-line treatment of locally advanced or metastatic adenocarcinoma of the pancreas. Oncology (Williston Park) 2007; 21:1696-706; discussion 706-9, 712, 715.

That which is claimed:

1. A pharmaceutical composition comprising:
a drug combination selected from gefitinib (ZD-1839 or ZD) and 74859 (S3I-201), Das and S3I-201, ZD and tyrphostin AG 490 (AG490), and dasatinib (Das) and AG490 in a pharmaceutically acceptable carrier.

2. The cytotoxic pharmaceutical composition of claim 1, further comprising gemcitabine.

3. A method of cytotoxically affecting pancreatic cancer cells in a host in need thereof, comprising:
contacting said pancreatic cells with a pharmaceutical composition comprising a drug combination that targets two or more cellular functional elements in pancreatic cancer cells selected from ZD and S3I-201, Das and S3I-201, ZD and AG490, and Das and AG490.

4. The method of claim 3, wherein two or more functional elements in pancreatic cancer cells comprise one of EGFR or Src and one of Stat3 or Jaks.

5. The method of claim 3, wherein the pharmaceutical composition further comprises gemcitabine.

6. The method of claim 3,
wherein the drug combination is ZD and S3I-201 and the two or more functional elements in pancreatic cancer cells comprise EGFR and Stat3,
wherein the drug combination is Das and S3I-201 and the two or more functional elements in pancreatic cells comprise Src and Stat3;
wherein the drug combination is ZD and AG490 and the two or more functional elements in pancreatic cancer cells comprise EGFR and Jaks, or
wherein the drug combination is Das and AG490 and the two or more functional elements in pancreatic cancer cells comprise Src and Jaks.

7. The method of claim 3, wherein the administration of a pharmaceutical composition suppresses c-myc expression in pancreatic cancer cells.

8. The method of claim 3, wherein the pharmaceutical composition further comprises a pharmaceutically acceptable carrier.

9. A method of making a pharmaceutical composition, comprising:
mixing a pharmaceutically acceptable carrier and a drug combination selected from ZD and S3I-201, Das and S3I-201, ZD and AG490, and Das and AG490.

10. The method of claim 9, wherein the pharmaceutical composition further comprises gemcitabine.

* * * * *

UNITED STATES PATENT AND TRADEMARK OFFICE
CERTIFICATE OF CORRECTION

PATENT NO. : 8,685,941 B2  Page 1 of 1
APPLICATION NO. : 13/131840
DATED : April 1, 2014
INVENTOR(S) : James Turkson It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 142 days.

Signed and Sealed this

Twenty-ninth Day of September, 2015

Michelle K. Lee
*Director of the United States Patent and Trademark Office*